United States Patent [19]

Tessier et al.

[11] Patent Number: 4,788,305
[45] Date of Patent: Nov. 29, 1988

[54] NOVEL RESOLUTION PROCESS

[75] Inventors: Jean Tessier, Vincennes; Jean-Pierre Demoute, Montreuil-sous Bois, both of France

[73] Assignee: Roussel Uclaf, Paris, France

[21] Appl. No.: 74,682

[22] Filed: Jul. 17, 1987

Related U.S. Application Data

[60] Division of Ser. No. 846,570, Mar. 31, 1986, Pat. No. 4,701,542, which is a continuation of Ser. No. 446,705, Dec. 3, 1982, abandoned.

[30] Foreign Application Priority Data

Dec. 9, 1981 [FR]  France ................................ 81 23003

[51] Int. Cl.$^4$ ............................................. C07D 307/77
[52] U.S. Cl. ..................................... 549/466; 549/330; 549/457; 549/458; 549/459; 549/463; 549/465; 549/456; 546/269; 558/424
[58] Field of Search ................ 549/330, 465, 466, 463, 549/457, 458, 459, 456

[56] References Cited

U.S. PATENT DOCUMENTS 4,701,542 10/1987 Tessien et al. ...................... 549/456

FOREIGN PATENT DOCUMENTS 0004493 10/1979 European Pat. Off. ............ 549/466

OTHER PUBLICATIONS

Chem Abstracts, vol. 99, 158225f (1983).
Boland et al., Chem. Ber. 110, pp. 1823 to 1832 (1977).
Maier et al., Chem. Ber. 101, pp. 1354 to 1370 (1968).
Gibson et al., J.A. C.S. 91, (17) pp. 4771 to 4778 (1969).
Grandguillot et al., Chem. Abst., vol. 92, 94/59 (1980).

Primary Examiner—Mary C. Lee
Assistant Examiner—J. Richter
Attorney, Agent, or Firm—Bierman & Muserlian

[57] ABSTRACT

Compounds of the formula

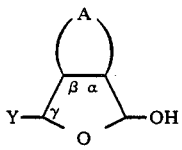

III wherein A is a hydrocarbon chain containing 1 to 16 groups, the said chain containing at least one heteroatom, at least one unsaturation, the assembly of the group constituting the chain may be a mono- or polycyclic system including a spiro or endosystem and the assembly of chain A and the carbon atoms attached thereto can contain at least one chiral atom or the hemiacetal moiety thereto which can present a chirality due to the dissymetric spatial configuration of the molecule and Y is selected from the group consisting of hydrogen, alkyl of 1 to 18 carbon atoms optionally substituted, —CY$_3'$ and the $\beta,\gamma$ bond together with Y can be part of A and Y' is bromine or chlorine.

4 Claims, No Drawings

NOVEL RESOLUTION PROCESS

This is a division of Ser. No. 846,570 filed Mar. 31, 1986, now U.S. Pat. No. 4,701,542, which is a continuation of application Ser. No. 446,705 filed Dec. 3, 1982, now abandoned.

STATE OF THE ART

French Pat. No. 2,383,927 describes substituted pyridyl esters of cyclopropane carboxylic acids but not with (S) or (R)α-cyano-(6-phenoxy-2-pyridyl)-methanol although it does describe the ester of the racemic alcohol. U.S. Pat. Nos. 4,218,469 and 4,261,920 describe racemic 4-fluoro-3-phenoxy-α-cyano-benzyl alcohol as ascertained from its formula and refractive index but not the (R) or (S) isomers. Copending, commonly assigned U.S. patent application Ser. No. 253,869 filed Apr. 13, 1981 describes a related resolution process.

OBJECTS OF THE INVENTION

It is an object of the invention to provide a novel resolution process.

It is a further object of the invention to provide novel isomers of the hemiacetals of formula III and certain alcohols.

These and other objects and advantages of the invention will become obvious from the following detailed description.

THE INVENTION

The novel process of the invention for the resolution of hemiacetal compounds of the formula

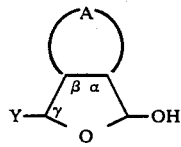   III wherein A is a hydrocarbon chain containing 1 to 16 groups; the said chain containing at least one heteroatom, at least one unsaturation, the assembly of the group constituting the chain may be a mono- or polycyclic system including a spiro or endosystem and the assembly of chain A and the carbon atoms attached thereto can contain at least one chiral atom or the hemiacetal moiety thereto which can present a chirality due to the dissymetric spatial configuration of the molecule and Y is selected from the group consisting of hydrogen, alkyl of 1 to 18 carbon atoms optionally substituted, —CY$_3$' and the $\beta$,  bond together with Y can be part of A and Y' is bromine or chlorine and the resolution of alcohols of the formula

R—OH     IV wherein R is selected from the group consisting of primary, secondary or tertiary alcohol moiety having at least one asymmetric carbon or the remainder of a substituted alcohol with a chirality due to the dissymetric spatial configuration of the entire molecule comprising reacting in an organic solvent diisobutyl aluminum hydride and a racemate or optical isomer of a compound of the formula

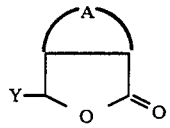   II wherein A and Y have the above definition to obtain a compound of the formula

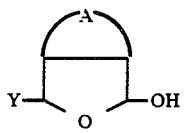   III and reacting the latter with a racemate or optical isomer of a compound of the formula

R—OH     IV wherein R has the above definition to obtain a compound of the formula

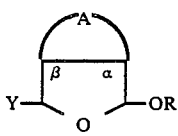   I wherein Y, A and R have the above definitions, separating the diastereoisomers and cleaving the latter to obtain the enantiomers of the hemiacetal of formula III if the racemate was used above or the alcohol of formula IV if the racemate was used above.

Examples of Y in the compounds of formula III are alkyl of 1 to 18 carbon atoms such as methyl, ethyl, propyl, isopropyl or branched or linear butyl, pentyl, hexyl, heptyl, octyl, nonyl or decyl; alkyl substituted with a halogen such as bromine or chlorine.

In the compounds of formula III, the two different groups which are substituents or asymetric centers in the A groups or the carbon atoms at which the claim A is attached may be methyl, ethyl, propyl, isopropyl or branched or linear butyl, pentyl, hexyl, heptyl, octyl, nonyl or decyl or taken with the carbon to which they are attached form cyclopropyl, cyclobutyl, cyclopentyl or cyclohexyl.

Among the compounds of formula III, particularly preferred are those whose different atoms or groups which substituent on carbon atoms containing chain A or situated in α- or β-position are individually selected from any of the following groups: (a) a member of the group consisting of hydrogen, halogens, nitro, alkyl of 1 to 18 carbon atoms, cycloalkyl of 3 to 6 carbon atoms, phenyl and phenyl substituted with at least one member of the group consisting of halogen and alkyl of 1 to 6 carbon atoms; (b) a member of the group consisting of —NH—R$_1$,

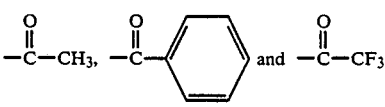

and $R_1$ is hydrogen or alkyl of 1 to 6 carbon atoms; (c)

wherein $R_2$ and $R_3$ are individually alkyl of 1 to 6 carbon atoms or taken together with the nitrogen atom form a 6-member heterocycle.

The alkyl substituents on the phenyl of (a) are preferably methyl, ethyl, propyl, isopropyl or branched or linear butyl, pentyl or hexyl. In the compounds of formula III, $R_1$, $R_2$ and $R_3$ are preferably methyl, ethyl, propyl, isopropyl or branched or linear butyl, pentyl or hexyl or $R_2$ and $R_3$ together with the nitrogen atom form a heterocycle selected from the group consisting of pyridinyl, pyridazinyl, pyrimidinyl, pyrazolinyl, piperazinyl, triazinyl and oxazinyl.

Among the compounds of formula III to be cited are those wherein the A group has a structure selected from the group consisting of

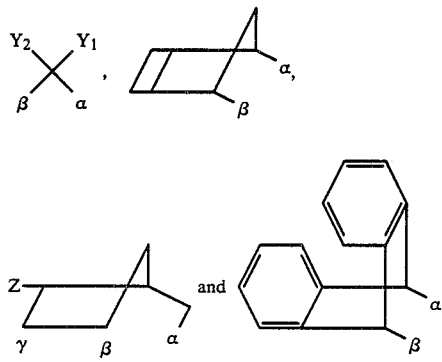

wherein $Y_1$ and $Y_2$ are individually selected from the group consisting of hydrogen, fluorine, chlorine, bromine and alkyl of 1 to 6 carbon atoms, especially both being methyl or $Y_1$ and $Y_2$ together with the carbon to which they are attached form a carbon homocycle of 3 to 7 carbon atoms and Z is selected from the group consisting of hydrogen, chlorine, bromine and iodine.

In the compounds of formula IV, R is a primary, secondary or tertiary alcohol moiety of aliphatic, cycloaliphatic or aromatic, mono or polycyclic type.

In the compounds of formula IV, R is a cyano methyl substituted group selected from the group consisting of α-cyano-3-phenoxy-benzyl, α-cyano-4-fluoro-3-phenoxy-benzyl and α-cyano-3-phenoxy-2-pyridyl-methyl. Also in the corresponding compounds of formula III, the cyano group may be replaced with alkyl, alkenyl or alkynyl of up to 6 carbon atoms.

Also among the compounds of formula IV are those wherein R is one of the following groups:

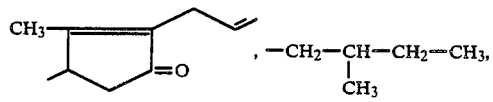

-continued

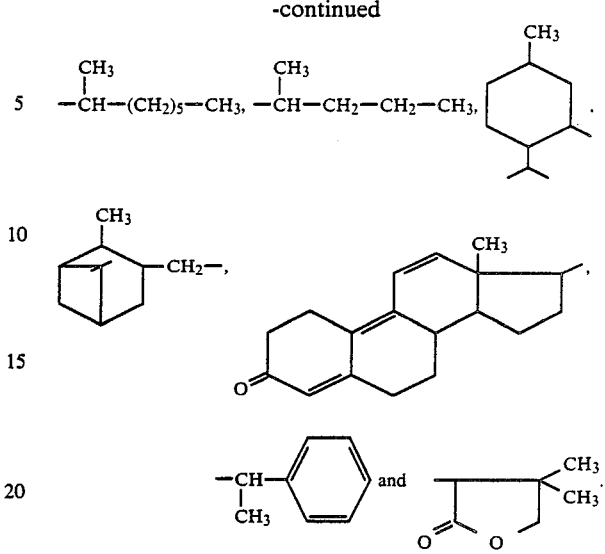

In the process of the invention, the organic solvent for the reaction of diisobutyl aluminum hydride and the compound of formula II is selected from the group consisting of aliphatic hydrocarbons, aromatic hydrocarbons and linear or cyclic ethers.

The reaction of the compounds of formula III and IV is preferably effected in the presence of an acid such as p-toluene sulfonic acid, methane sulfonic acid, hydrochloric acid, sulfuric acid, phosphoric acid, m-nitrobenzene sulfonic acid, 5-sulfosalicylic acid and camphosulfonic acid and is effected in an organic solvent selected from the group consisting of aliphatic hydrocarbons, aromatic hydrocarbons, ethers, chlorinated hydrocarbons and aliphatic ketones.

The water formed by the condensation of the alcohol and the hemiacetal compound is preferably eliminated by azeotropic entrainment at reflux of a solvent selected from the group consisting of chlorinated solvents, aromatic hydrocarbons, aliphatic hydrocarbons and ethers.

The separation of the diastereoisomers of formula I may be effected by crystallization of chromatography. The cleavage of the diasteroisomers may be effected in a mixture of dioxane and water with p-toluene sulfonic acid.

In a preferred embodiment of the process of the invention where Y is hydrogen, a compound of the formula

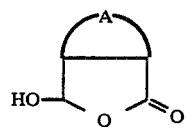

V is reacted with an alkali metal borohydride in a solvent and then with an acid in an organic solvent to obtain a compound of the formula

$II_A$ which was reacted as described above.

The compounds of formula V are described in French Pat. No. 2,423,488. Where Y is —CCl₃ or —CBr₃, the starting compounds of formula II are described in French Pat. No. 2,396,006.

In a preferred mode of the process to prepare a compound of formula II$_A$, the alkali metal borohydride is reacted in a solvent selected from the group consisting of water, dimethylformamide or an aliphatic alcohol. The acid is preferably p-toluene sulfonic acid and the organic solvent is selected from the group consisting of benzene, xylene and toluene.

In a preferred embodiment of the resolution process of the invention, the alcohol of formula IV is racemic and selected from the group consisting of (R,S)α-cyano-3-phenoxy-benzyl alcohol, (R,S)α-cyano-4-fluoro-3-phenoxy-benzyl alcohol, (R,S)α-cyano-(6-phenoxy-2-pyridyl)methyl alcohol and (R,S)allethrolone.

The compounds of formula III are novel compounds and are necessary intermediates for the process of the invention. Especially preferred are the compounds of formula III produced in the Examples. The compounds of formula I produced by the process of the invention are also novel compounds.

Certain of the resolved alcohols of formula IV are new, especially (S)α-cyano-4-fluoro-3-phenoxy-benzyl alcohol, (R)α-cyano-4-fluoro-3-phenoxy-benzylalcohol, (S)α-cyano-(6-phenoxy-2-pyridyl)-methanol and (R)α-cyano-(6-phenoxy-2-pyridyl)methanol.

As can be clearly seen from the working examples, the process of the invention is a method of resolving compounds of formulae III and IV in a remarkable manner. The process particularly permits the resolution of very fragile alcohols such as cyanohydrins and it is also possible to resolve certain cyanohydrins not previously capable of being resolved such as α-cyano-4-fluoro-3-phenoxy-benzyl alcohol and α-cyano-(6-phenoxy-2-pyridyl)methanol.

The resolution process of alcohols can be schematically illustrated as follows:

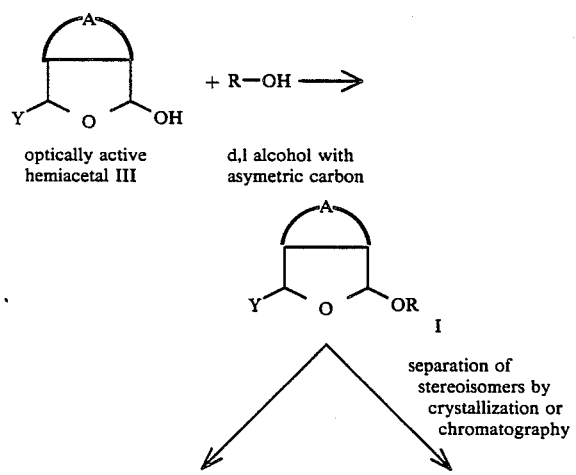

-continued

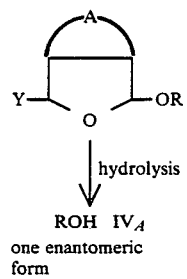

ROH IV$_A$
one enantiomeric form

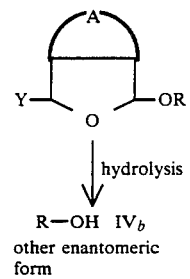

R—OH IV$_b$
other enantiomeric form

The resolution of the compounds of formula III can be schematically illustrated in an analogous manner.

The method of the invention is not limited to the resolution of compounds of formulae III and IV especially but on the contrary, it is a very general method capable of resolving a very large number of compounds in excellent yields using simple reactions under mild conditions.

In the following examples there are described several preferred embodiments to illustrate the invention. However, it should be understood that the invention is not intended to be limited to the specific embodiments.

EXAMPLE 1

(1R,2R,5S) 6,6-dimethyl-3-oxa-2-[(S) cyano-(3-phenoxy-phenyl)-methoxy]-bicyclo (3,1,0) hexane [produce A] and (1R,2R,5S) 6,6-dimethyl-3-oxa-2-[(R) cyano-(3-phenoxy-phenyl)-methoxy]-bicyclo (3,1,0) hexane [product B]

STEP A: (1R,5S) 6,6-dimethyl-3-oxa-bicyclo (3,1,0) hexane-2-one 170.6 g of (1R,5S) 6,6-dimethyl-b 4-(R)-hydroxy-3-oxa-bicyclo (3,1,0) hexane-2-one were added to 800 ml of water and a solution of 127.2 g of sodium carbonate in 400 ml of water was slowly added thereto at 0° C. The mixture was stirred at 0° C. for 15 minutes and 45.4 g of sodium borohydride were added thereto at 0° C. in small fractions. The mixture was stirred for 4 hours at 0° C. and adjusted to a pH of 2 by addition of 2N hydrochloric acid. The mixture was saturated with sodium chloride and stood overnight and was extracted with methylene chloride. The extract was evaporated to dryness under reduced pressure and the residue was rectified under reduced pressure to obtain 130.2 g of (1R,5S) 6,6-dimethyl-3-oxa-bicylo (3,1,0) hexane-2-one with a specific rotation of $[\alpha]_D^{20} = -92°$ (c=1% in ethanol.

STEP B: (1R,2S,5S) 6,6-dimethyl-3-oxa-bicyclo (3,1,0) hexane-2-ol 404 ml of a toluene solution of 1.2 moles of diisobutyl aluminum hydride were slowly added at −70° C. to a solution of 60 g of the product of Step A in 720 ml of toluene and the mixture was stirred at −65° C. for 16 minutes and slowly poured into an aqueous solution of sodium potassium tartrate. The mixture was stirred and allowed to stand and the decanted aqueous phase was extracted with ether. The combined organic phases were evaporated to dryness and the residue was taken up in methylene chloride. The solution was evaporated to dryness under reduced pressure to obtain 56.7 g of (1R,2S,5S) 6,6-dimethyl-3-oxa-bicyclo (3,1,0) hexane-2- ol with a boiling point of ≃50° C. at 0.5 mm Hg and a specific rotation of $[\alpha]_D^{20} = +66.5°$ (c=1% in ethanol).

STEP C: (1R,2R,5S) 6,6-dimethyl-3-oxa-2-[(S) or (R) cyano-(3-phenoxy-phenyl)-methoxyl]-bicyclo (3,1,0) hexane A mixture of 410 mg of (R,S)α-cyano-3-phenoxybenzyl alcohol, 256 mg of the product of Step B, 10 ml of methylene chloride and 15 mg of p-toluene sulfonic acid was refluxed for 30 minutes and cooled. The mixture was evaporated to dryness under reduced pressure and the residue was chromatographed over silica gel. Elution with benzene yielded 461 mg of (1R,2R,5S) 6,6-dimethyl-3-oxa-2-[(R,S) cyano-(3-phenoxy-phenyl)-methoxy]-bicyclo (3,1,0) hexane and the said product was added to a mixture of 2.5 ml of isopropanol, 0.2 ml of water and 1 drop of triethylamine. The mixture was chromatographed to obtain a few crystals of the (S) isomer which were stirred at room temperature for 17 hours. The mixture was stirred at 0° to 5° C. and was vacuum filtered to obtain 105 mg of (1R,2R,5S) 6,6-dimethyl-3oxa-2-[(S) cyano-3-phenoxy-phenyl)-methoxy]-bicyclo (3,1,0) hexane melting at 70° C. and having a specific rotation of $[\alpha]_D^{20} = +78° \pm 1.5°$ (c=1% in benzene). By chromatography of the product at the beginning of the Step and elution with benzene, there was obtain the corresponding (R) isomer of (Product B).

| Circular Dichroism: | | |
| --- | --- | --- |
| Product A: | max. at 263 nm | Δε = +0.10 |
| | max. at 275 nm | Δε = −0.19 |
| | max. at 287 nm | Δε = +0.10 |
| Product B: | max. towards 235 nm | Δε = +3 |
| | max. at 277 nm | Δε −0.1 |
| | max. at 285 nm | Δε = −0.2 |

NMR Spectrum (deuterochloroform):

Product A: Peaks at 1 ppm (hydrogens of geminal methyls); at 1.42–1.67 ppm (hydrogens of cyclopropane); at 3.7–4.7 ppm (4α-hydrogen of lactol); at 4.1–4.2 ppm (4β-hydrogen of lactol); at 4.9–5.3 ppm (2-hydrogen of lactol and hydrogen of carbon attached to —CN); at 6.8–7.5 ppm (aromatic hydrogens).

Product B: Peaks at 1.04 ppm (hydrogens of geminal methyls); at 1.48–1.7 ppm (hydrogens of isopropyl); at 3.9–4.1 ppm (4-hydrogens of hemiacetal ring); at 5.2–5.5 ppm (2-hydrogen of hemiacetal and hydrogen of carbon attached to —CN); at 6.8–8.1 ppm (aromatic hydrogens).

EXAMPLE 2

(1R,2R,4R,5S) 6,6-dimethyl-3-oxa-2-[(S) or (R) cyano-(3-phenoxy-phenyl)-methoxy]-4-(2-methyl-2-propyl)-bicyclo (3,1,0) hexane STEP A: (1R,cis) 2,2-dimethyl-3-(1-hydroxy-2,2-dimethylpropyl)-cyclopropane-carboxylic acid 46 ml of a solution of 1.5M of tert.-butyllithium in pentane were slowly added at −70° C. to a mixture of 5 g of (1R,cis) 6,6-dimethyl-3-oxa-4R-hydroxy-bicyclo (3,1,0) hexane-2-one and 50 ml of tetrahydrofuran and the mixture was stirred for one hour and was poured into aqueous monosodium phosphate solution. The mixture was extracted with methylene chloride and the extract was evaporated to dryness under reduced pressure. The residue was chromatographed over silica gel and was eluted with a 1-1 benzene-ethyl acetate mixture to obtain (1R,cis) 2,2-dimethyl-3-(1-hydroxy-2,2-dimethylpropyl)-cyclopropane-carboxylic acid melting at 129° C.

STEP B: (1R,4R,5S) 6,6-dimethyl-4-(2-methyl-prop-2-yl)-3-oxa-bicyclo (3,1,0) hexan-2-one A solution of 5 g of the product of Step A in 50 ml of benzene was heated to reflux and 20 mg of p-toluene sulfonic acid were added thereto and reflux was continued for 15 minutes. The mixture was cooled and was washed with aqueous sodium hydroxide and evaporated to dryness under reduced pressure. The residue was chromatographed over silica gel and was eluted with a 9-1 benzene-ethyl acetate mixture to obtain (1R,4R,5S) 6,6-dimethyl-4-(2-methyl-prop-2-yl)-3-oxa-bicyclo (3,1,0) hexan-2-one melting at 113° C.

STEP C: (1R,2R,4R,5S) 6,6-dimethyl-4-(2-methyl-prop-2-yl)-3-oxa-bicyclo (3,1,0) hexan-2-ol 15.5 ml of a toluene solution of 20% of diisobutyl aluminum hydride were slowly added at −70° C. to a solution of 2.5 g of the product of Step B in 25 ml of toluene with stirring and the mixture was poured over ice. The mixture was filtered and the filtrate was extracted with ether and was evaporated to dryness under reduced pressure to obtain 2.5 g of (1R,2R,4R,5S) 6,6-dimethyl-4-(2-methyl-prop-2-yl)-3-oxa-bicyclo (3,1,0) hexan-2-ol melting at 126° C.

STEP D: (1R,2R,4R,5S) 6,6-dimethyl-3-oxa-2-[(S) or (R)-3-phenoxy-phenyl)-methoxy]-4-(2-methyl-2-propyl)-bicyclo (3,1,0) hexane A mixture of 2 g of the product of Step C, 30 ml of benzene, 2.5 g of (R,S) α-cyano-3-phenoxy-benzyl alcohol and 10 mg of p-toluene sulfonic acid was stirred at 20° C. for 20 hours and was washed with aqueous sodium bicarbonate and evaporated to dryness under reduced pressure. The residue was chromatographed over silica gel and was eluted with a 9-1 petroleum ether (b.p.=35°–70° C.)-ether mixture to obtain 1.15 g of (1R,2R,4R,5S) 6,6-dimethyl-3-oxa-2-[(S) cyano-(3-phenoxy-phenyl)-methoxy]-4-(2-methyl-2-propyl)-bicyclo (3,1,0) hexane [product B] and 0.600 g of the corresponding (R) isomer [Product B].

NMR Spectrum (deutderochloroform):

Product A: Peaks at 0.85 ppm (hydrogens of methyls of tert.-butyl); at 1.06 ppm (hydrogens of geminal methyls); at 1.25 to 1.72 ppm (hydrogens of cyclopropyl); at 3.6 ppm (hydrogen of -O-CH-tert.-butyl); at 5.2–5.4 ppm (hydrogens of —OCH—O and —CH—CN).

Product B: Peaks at 1.025 ppm (hydrogens of methyls of tert.-butyl); at 0.97–1.07 ppm (hydrogens of geminal methyls); at 1.33–1.45 ppm and 1.53–1.65 ppm (hydrogens of cyclopropyl); at 3.6 ppm (hydrogen of -OCH-tert.-butyl); at 4.8–5.4 ppm (hydrogens of —OCHO and —CH—CN).

EXAMPLE 3

1R,2S,4R,5S) 6,6-dimethyl-4-trichloro-methyl-2-(1-(S) or [(R)-2-methyl-4-oxo-3-(2-propen-1-yl)-cyclopent-2-eny]-3-oxa-bicyclo (3,1,0) hexane

STEP A: (1R,2S,4R,5S) 6,6-dimethyl-4-trichloromethyl-3-oxa-bicyclo (3,1,0) hexan-2-ol 75 ml of toluene solution of 20% of diisobutyl-aluminum hydride were slowly added at −60° C. to a solution of 20 g of (1R,4R,5S) 6,6-dimethyl-4-trichloromethyl-3-oxa-bicyclo (3,1,0)-hexane-2-one in 200 ml of toluene and the mixture was stirred at −60° C. for one hour and was poured into an ice-water mixture. Aqueous N hydrochloric acid was added to the mixture to adjust the pH to 3 to 4 and the mixture was filtered. The decanted benzene phase was washed with aqueous sodium bicarbonate solution, with water and evaporated to dryness under reduced pressure. The residue was added to petroleum ether (b.p.=35°-70° C.) and the mixture was filtered to obtain 14.5 g of (1R,2S,4R,5S) 6,6-dimethyl-4-trichloromethyl-3-oxa-bicyclo (3,1,0) hexan-2-ol melting at 140° C.

STEP B: (1R,2S,4R,5S) 6,6-dimethyl-4-trichloromethyl-2-[1(R) or 1(S) 2-methyl-4-oxo-3-(2-propen-1-yl)-cyclopent-2-enyloxy]-3-oxo-bicyclo (3,1,0) hexane A mixture of 3.21 g of (R,S) allethrolone, 40 mg of p-toluene sulfonic acid, 0.800 g of the product of Step A and 40 ml of methylene chloride was refluxed in a Dean-Stark apparatus, garnied with anhydrous aluminum gel and 4 times the same quantity of lactol was added thereto every half hour for 4 g of lactol. The mixture was refluxed for 4 hours and was then washed with aqueous sodium bicarbonate solution, then with water. The organic phase was evaporated to dryness under reduced pressure and water was added to the residue. The mixture was filtered. Actone was added to the filtrate and the mixture was filtered. The acetone filtrate was evaporated to dryness and methylene chloride was added to the residue. The organic solution was washed with water and evaporated to dryness under reduced pressure. The residue was added to isopropyl ether at 50° C. and the mixture stood overnight at 20° C. and was then cooled to 0° C. and vacuum filtered. The product was dried and dissolved in methylene chloride. The solution was filtered and the filtrate was evaporated to dryness under reduced pressure. The residue was dissolved at 50° C. in isopropyl ether and the solution stood at 20° C. for one hour and was vacuum filtered to obtain 1.82 g of (1R,2S,4R,5S) 6,6-dimethyl-4-trichloromethyl-2-[1(R) 2-methyl-4-oxo-3-(2-propen-1-yl)-cyclopent-2-enyloxy]-3-oxa-bicyclo (3,1,0) hexane [Product A] melting at 128°-130° C. The crystallization mother liquors and recrystallization were evaporated to dryness under reduced pressure and the residue was crystallized from isopropyl ether to obtain 2.67 g of the corresponding 1(S) isomer [Product B].

EXAMPLE 4

(1R,2S,4R,5S) 6,6-dimethyl-4-tribromomethyl-2-[1(R) 2-methyl-4-oxo-3-(2-propen-1-yl)-cyclopent-2-enyloxy]-3-oxa-bicyclo (3,1,0) hexane

STEP A: (1R,5S) 6,6-dimethyl-4(R)-tribromomethyl-3-oxa-bicyclo (3,1,0) hexan-2(S)-ol 50 ml of a 20% solution of diisobutyl aluminum hydride in toluene were slowly added at −60° C. to a mixture of 20 g of (1R,5S) 6,6-dimethyl-4(R)-tribromomethyl-3-oxa-bicyclo (3,1,0) hexan-2-one in 200 ml of toluene and the mixture was stirred for one hour at −60° C. and was poured into a mixture of ice and N hydrochloric acid solution. The temperature rose to 20° C. and the mixture was filtered. The decanted organic phase of the filtrate was washed with aqueous sodium bicarbonate solution, with water and evaporated to dryness under reduced pressure to obtain 17.6 g of (1R,5S) 6,6-dimethyl-4(R)-tribromomethyl-3-oxo-bicyclo (3,1,0) hexan-2(S)-ol.

STEP B: (1R,2S,4R,5S) 6,6-dimethyl-4-tribromomethyl-2-[1(R) 2-methyl-4-oxo-3-(2-propen-1-yl)-cyclopent-2-enyloxy]-3-oxa-bicyclo (3,1,0) hexane A mixture of 0.8 g of (R,S) allethrolone, 2 g of the product of Step A, 20 mg of p-toluene sulfonic acid and 20 ml of methylene chloride was refluxed for 4 hours and then stood at 20° C. for 16 hours and was filtered. The filtrate was evaporated to dryness under reduced pressure and the residue was taken up in a 8-2 petroleum ether (b.p.=35°-70° C.)-ether mixture. The mixture was filtered and the filtrate was evaporated to dryness under reduced pressure. The residue was added to petroleum ether (b.p.=35° to 70° C.) and the mixture was vacuum filtered to obtain 0.726 g of (1R,2S,4R,5S) 6,6-dimethyl-4-tribromomethyl-2-[1(R) 2-methyl-4-oxo-3-(2-propen-1-yl)-cyclopent-2-enyloxy]-3-oxa-bicyclo (3,1,0) hexane melting at 126°-128° C. and having a specific rotation of $[\alpha]_D^{20} = +37.5°$ C. (c=1% in benzene).

EXAMPLE 5

(3aR,4R,7S,7aS,1R) 1-[R or S cyano-(3-phenoxy-phenyl)-methoxy]-tetrahydro-4,7-methano-isobenzofurane

STEP A: Racemic 1-hydroxy-3-oxo-1,3,3a,7a-tetrahydro-4,7-methano-isobenzofuran 244 ml of cyclopentadiene were slowly added to a mixture of 208 g of 5-hydroxy-2(5H)-furanone, 350 mg of hydroquinone and 1.05 liters of chloroform while keeping the temperature at 45°-47° C. and the mixture was stirred at 20° C. for 17 hours and was evaporated to dryness under reduced pressure. The residue was added to isopropyl ether and the mixture was heated to reflux with stirring and was cooled and vacuum filtered. The solid was dissolved in methylene chloride and the solution was treated with activated carbon and evaporated to dryness under reduced pressure. The residue and isopropyl ether was heated to reflux with stirring and was cooled and vacuum filtered to obtain 325.7 g of racemic 1-hydroxy-3-oxo-1,3,3a,7a-tetrahydro-4,7-methanoisobenzofuran melting at 105° C.

STEP B: (3R,3aR,4R,7S,7aS) 3-[1(S) 2-methyl-4-oxo-3-(propen-1-yl)-cyclopent-2-enyloxy]-tetrahydro-4,7-methano-isobenzofuran-1-one A mixture of 54 g of (S) allethrolone, 55.7 g of the product of Step A, 6.75 g of p-toluene sulfonic acid and 350 ml of benzene was heated to reflux and evaporated to dryness under reduced pressure. The residue was added to isopropyl ether and the mixture was vacuum filtered to obtain 36.5 g of (3R,3aR,4R,7S,7aS) 3-[1-(S) 2-methyl-4-oxo-3-(propen-1-yl)-cyclopent-2-enyloxy]-tetrahydro-4,7-methano-isobenzofuran-1-one melting at 148° C. and having a specific rotation of $[\alpha]_D^{20} = -8.5°$ (c=1% in benzene). Chromatography of the mothers liquors yielded another 12.3 g of the said product melting at 145° C.

STEP C: (3R,3aR,4R,7S,7aS) 3-hydroxy-tetrahydro-4,7-methano-isobenzofuran-1-one A mixture of 35.5 g of the product of Step B, 3.5 g of p-toluene sulfonic acid, 355 ml of water and 188 ml of dioxane was refluxed for 2 hours and 4 ml of triethylamine were added to the solution to adjust the pH to 7. The mixture was evaporated to dryness under reduced pressure to obtain 8.5 g of (3R,3aR,4R,7S,7aS) 3-hydroxy-tetrahydro-4,7-methano-isobenzofuran-1-one melting at 120° C.

STEP D: (3aR,4R,7S,7aS) tetrahydro-4,7-methano-isobenzofuran-1-one 0.7 g of sodium borohydride were slowly added at 0° C. to a mixture of 3 g of the product of Step C and 30 ml of water and the mixture was stirred until all of the starting material had reacted. N hydrochloric acid was added to the mixture to adjust the pH to 2 and the mixture was extracted with methylene chloride. The organic phase was evaporated to dryness under reduced pressure and the residue was added to benzene and 50 mg of p-toluene sulfonic acid. The mixture was held at 30° C. for 30 minutes and was then evaporated to dryness under reduced pressure. The residue was crystallized from isopropyl ether to obtain 1.9 g of (3aR,4R,7S,7aS) tetrahydro-4,7-methano-isobenzofuran-1-one melting at 131° C.

STEP E: (3aR,4R,7S,7aS,1S) tetrahydro-4,7-methano-isobenzofuran-1-ol 33 ml of a solution of 1.2M of diisobutyl aluminum hydride in toluene were slowly added at −70° C. to a mixture of 5.6 g of the product of Step D and 50 ml of toluene and the mixture was poured over ice. The mixture was stirred with a 1M solution of sodium potassium double tartrate and the decanted aqueous phase was extracted with methylene chloride after being saturated with sodium chloride. The combined organic phases were evaporated to dryness under reduced pressure and the residue was chromatographed over silica gel. Elution with a 1-1 petroleum ether (b.p.=35°-75° C.)-ethyl acetate mixture yielded 5.3 g of (3aR,4R,7S,7aS,1S) tetrahydro-4,7-methano-isobenzofuran-1-one melting at 100° C. and having a specific rotation of $[\alpha]_D^{20} = +53.5°$ (c=1% in benzene).

STEP F: (3aR,4R,7S,7aS,1R) 1-[(R) or (S) cyano-(3-phenoxy-phenyl)-methoxy]-tetrahydro-4,7-methano-isobenzofuran 4.2 g of the product of Step E were added in small fractions with stirring to a mixture of 8.1 g (R,S)α-cyano-3-phenoxy-benzyl alcohol, 80 mg of p-toluene sulfonic acid and 70 ml of methylene chloride and the mixture was stirred for 15 minutes and evaporated to dryness under reduced pressure. The residue was chromatographed over silica gel and eluted with a 95-5 benzene-ethyl acetate mixture. The product was again chromatographed over silica gel and eluted with a 3-1 petroleum ether (b.p.=40°-70° C.)-ether mixture to obtain 4 g of (3aR,4R,7S,7aS,1R) 1-[R-(cyano-3-phenoxy-phenyl)-methoxy-tetrahydro-4,7-methano-isobenzofuran [product A] and 3.5 g of the corresponding S isomer [product B].

NMR Spectrum (deuterochloroform):

Product A: Peaks at 3.4 to 4 ppm (hydrogens of —OCH$_2$—); at 5.0-5.4 ppm (hydrogen of

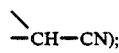

at 6.2 ppm (ethylenic hydrogens); at 6.8 to 7.5 ppm (aromatic hydrogens).

Product B: Peaks at 3.5-3.6 ppm (hydrogens of —CH$_2$—O—); at 5.2 ppm (hydrogen of

at 5.9 to 6.3 ppm (ethylenic hydrogens); at 6.8 to 7.5 ppm (aromatic hydrogens).

EXAMPLE 6

(11R,12S,15S) or (11S,12R,15R) 12-[(S) cyano-(3-phenoxy-phenyl)-methoxy]-9,10,11,12,14,15-hexahydro-9,10 [3',4']-furano-anthracene

STEP A: Racemic 9,10,14,15-tetrahydro-9,10-[3,',4']-furano-anthracene-12(11H)-one A mixture of 1 g of anthracene and 1.5 g of 2(5H)-furanone was heated with stirring at 170° C. for 17 hours and was then cooled and methylene chloride was added thereto. The mixture was treated with active carbon and was filtered and the filtrate was evaporated to dryness under reduced pressure. The residue was chromatographed over silica gel and was eluted with a 95-5 benzene-ethyl acetate mixture to obtain 1.2 g of racemic 9,10,14,15-tetrahydro-9,10-[3',4']-furano-anthracene-12 (11H)-one melting at 231° C.

STEP B: Racemic 9,10,11,12,14,15-hexahydro-9,10-[3',4']-furano-anthracene-12-ol 18 ml of a 1.2M solution of diisobutyllithium in toluene were slowly added to a mixture of 5 g of the product of step A in 70 ml of tetrahydrofuran and the mixture was poured into a mixture of ice and aqueous N hydrochloric acid solution. The mixture was extracted with benzene and the organic phase was washed with water and evaporated to dryness under reduced pressure. The residue was crystallized from isopropyl ether to obtain 4.7 g of racemic 9,10,11,12,14,15-hexahydro-9,10-[3',4']-furano-anthracene-12-ol melting at 187° C.

STEP C: (11R,12S,15S) and (11S,12R,15R) 12-[(S) cyano-(3-phenoxy-phenyl)-methoxy]-9,10,11,12,14,15-hexahydro-9,10 [3',4']-furano-anthracene A mixture of 12.5 g of (S)α-cyano-3-phenoxy-benzyl alcohol, 100 mg of p-toluene sulfonic acid and 100 ml of methylene chloride was heated to reflux while 8.0 g of the product of Step B were slowly added thereto in small fractions and the mixture was refluxed for 30 minutes and was cooled. The mixture was washed with water and evaporated to dryness under reduced pressure. The residue was taken up in isopropyl ehter and the mixture was stirred for 17 hours and was vacuum filtered. The filtrate was evaporated to dryness and the residue was added to a 2-1 methanol-water mixture. The mixture was extracted with heptane and the heptane extract and the crystals from the filtration were chromatographed over silica gel. Elution with benzene yielded 6.8 g of (11R,12S,15S) 12-[(S)cyano-(3-phenoxy-phenyl)-methoxy]-9,10,11,12,14,15-hexahydro-9,10-[3',4']furano-anthracene melting at 178° C. and having a specific rotation of $[\alpha]_D^{20} = -119°$ (c=1% in carbon tetrachloride) and 6.1 g of the corresponding (11S,12R,15R) isomer melting at 167° C. and having a specific rotation of $[\alpha]_D^{20} = +111°$ (c=1% in carbon tetrachloride).

EXAMPLE 7

(11R,12S,15S) and (11S,12R,15R) 12-[(R)(4,4-dimethyl-2-oxo-tetrahydrofuran-3-yl)-oxy]-9,10,11,12,14,15-hexahydro-9,10[3',4']-furano-anthracene STEP A: (11R,12S,15S) and (11S,12R,15R) 12-[(1R,2S,5R) 2-prop-3-yl-5-methyl-cyclohexyloxy]-9,10,11,12,14,15-hexahydro-9,10[3',4']-furano-anthracene 5 g of racemic 9,10,11,12,14,15-hexahydro-9,10[3',4']-furano anthracene-12-ol were slowly added to a refluxing solution of 4.2 g of 1-methanol, 100 ml of methylene chloride and 100 mg of p-toluene sulfonic acid and the mixture was cooled to room temperature and was diluted with water. The mixture was extracted with methylene chloride and the organic phase was washed with aqueous sodium bicarbonate solution, dried and evaporated to dryness under reduced pressure. The residue was chromatographed over silica gel and eluted with a 7-3 benzene-petroleum ether (b.p.=40°-70° C.) mixture to obtain 2.9 g of (11R,12S,15S) 12-[(1R,2S,5R)-2-prop-2-yl-5-methyl-cyclohexyloxy]-9,10,11,12,14,15-hexahydro-9,10[3',4']furano-anthracene melting at 180° C. and having a specific rotation of $[\alpha]_D^{20} = -144°$ (c=1% in dimethylformamide) and 2.5 g of the corresponding (11S,12R,15R) isomer melting at 170° C. and having a specific rotation of $[\alpha]_D^{20} = +50°$ (c=1% in dimethylformamide).

STEP B: (11R,12R,15S) 9,10,11,12,14,15-hexahydro-9,10[3',4']-furano-anthracene-12-ol A mixture of 2.5 g of the (11S,12R,15R) isomer of Step A, 30 ml of dioxane, 20 ml of water and 250 mg of p-toluene sulfonic acid was heated to reflux and then was cooled to room temperature and was diluted with water. The mixture was extracted with water and the organic phase was washed with aqueous saturated sodium chloride solution, then with water, dried and evaporated to dryness under reduced pressure. The residue was chromatographed over silica gel and eluted with a 7-3 cyclohexane-ethyl acetate mixture and then with a 1-1 cyclohexane-ethyl acetate mixture to obtain 1.5 g of (11R,12R,15S) 9,10,11,12,14,15-hexahydro-9,10[3',4']furano-anthracene-12-ol melting at 160° C. and having a specific rotation of $[\alpha]_D^{20} = -44°$ (c=0.9% in dimethylformamide).

STEP C: (11R,12S,15S) and (11S,12R,15R) 12-[(R)(4,4-dimethyl-2-oxo-tetrahydrofuran-3-yl)-oxy]-9,10,11,12,14,15-hexahydro-9,10-[3',4']furano-anthracene A solution of 2.5 g of the product of Step B in 25 ml of methylene chloride was slowly added to a refluxing mixture of 1.8 g of racemic 4,4-dimethyl-2-oxo-3-hydroxy-tetrahydrofuran, 20 ml of methylene chloride and 180 mg of p-toluene sulfonic acid and the mixture was refluxed for one hour and was allowed to cool to room temperature. The mixture was washed with aqueous sodium bicarbonate solution, with water, dried and evaporated to dryness under reduced pressure. The residue was chromatographed over silica gel and was eluted with a 9-1 toluene-ethyl acetate mixture to obtain 1.7 g of (11S,12S,15S) 12-[(R)(4,4-dimethyl-2-oxo-tetrahydrofuran-3-yl)-oxy]-9,10,11,12,14,15-hexahydro-9,10[3',4']furano-anthracene melting at 216° C. and having a specific rotation of $[\alpha]_D^{20} = -115°\pm2.5°$ (c=1% in dimethylformamide) and 1.55 g of the corresponding (11S,12R,15R) isomer melting at 270° C. and having a specific rotation of $[\alpha]_D^{20} = -89.5°\pm3°$ (c=0.5% in dimethylformamide).

EXAMPLE 8

(11S,12R,15R) 12-[(R) and (S)cyano-(3-phenoxy-phenyl)-methoxy]-9,10,11,12,14,15-hexahydro-9,10[3',4']-furano-anthracene STEP A: (11S,12S,15R) 9,10,11,12,14,15-hexahydro-9,10[3',4']-furano-anthracene-12-ol A mixture of 2.8 g of (11S,12R,15R) 12-[(1R,2S,5R)-2-prop-2-yl-5-methyl-cyclohexyloxy]-9,10,11,12,14,15-hexahydro-9,10-[3',4']furano-anthracene prepared in Step A of Example 7, 40 ml of dioxane, 20 ml of water and 300 mg of p-toluene sulfonic acid was heated to reflux and allowed to cool to room temperature and was diluted with water. The mixture was extracted with methylene chloride and the organic phase was washed with aqueous saturated sodium bicarbonate solution, with water, dried and evaporated to dryness under reduced pressure. The residue was chromatographed over silica gel and was eluted with a 7-3 cyclohexane-ethyl acetate mixture and then with a 1-1 cyclohexane-ethyl acetate mixture to obtain 1.7 g of (11S,12S,15R) 9,10,11,13,14,15-hexahydro-9,10[3',4']furano-anthracene-12-ol melting at 160° C. and having a specific rotation of $[\alpha]_D^{20} = +41°$ (c=1% in dimethylformamide).

STEP B: (11S,12R,15R) 12-[1(R) and (S)cyano-(3-phenoxy-phenyl)-methoxy]-9,10,11,12,14,15-hexahydro-9,10[3',4']-furano-anthracene A mixture of 1.5 g of (R,S)α-cyano-3-phenoxy-benzyl alcohol, 30 ml of methylene chloride and 150 mg of p-toluene sulfonic acid was heated to reflux and a solution of 1.3 g of the product of Step A in 20 ml of methylene chloride were added thereto. The mixture was cooled to room temperature and was washed with aqueous sodium bicarbonate solution, with water, dried and evaporated to dryness under reduced pressure. The residue was chromatographed over silica gel and was eluted with benzene to obtain 1.05 g of (11S,12R,15R) 12-[(1R)cyano-(3-phenoxy-phenyl)-methoxy]-9,10,11,12,14,15-hexahydro-9,10-[3′,4′]furano-anthracene melting at 178° C. and having a specific rotation of $[\alpha]_D^{20} = +122°$ (c=1% in CCl$_4$) and 960 mg of the corresponding (1S) isomer melting at 167° C. and having a specific rotation of $[\alpha]_D^{20} = +111°$ (c=1% in CCl$_4$).

EXAMPLE 9

(2R) and (2S)(6-bromo-hexahydro-3,5-methano-2H-cyclopenta[b]furan-2-yl)-oxy-(S)α-cyano-3-phenoxy-benzyl STEP A: Racemic 6-bromo-hexahydro-3,5-methano-2H-cyclopenta[b]furan-2-ol 275 ml of a toluene solution of 1.2M of diisobutyl aluminium hydride were slowly added at −60° C. to a mixture of 62.16 g of 6-bromo-hexahydro-3,5-methano-2H-cyclopenta[b]furan-2-one [prepared by method of Ver Nooy et al, J.A.C.S., Vol. 77 (1955), p. 3583] and 500 ml of toluene and the mixture was stirred at −60° C. for 45 minutes and was then poured into aqueous 1M sodium potassium double tartrate. The mixture was stirred for 2 hours and the decanted aqueous phase was saturated with sodium chloride and extracted with methylene chloride. The combined organic phases were evaporated to dryness under reduced pressure to obtain 64.7 g of racemic 6-bromo-hexahydro-3,5-methano-2H-cyclopenta[b]furan-2-ol melting at 104° C.

STEP B: (2R) and (2S)(6-bromo-hexahydro-3,5-methano-2H-cyclopenta[b]furan-2-yl)-oxy (S)α-cyano-3-phenoxy-benzyl A mixture of 8.79 g of (S)α-cyano-3-phenoxy-benzyl alcohol, 200 ml of methylene chloride and 880 mg of p-toluene sulfonic acid was refluxed with stirring while adding a solution of 6.57 g of the product of Step A in 150 ml of methylene chloride over 90 minutes and the mixture was refluxed with stirring for another 15 minutes and was allowed to cool to room temperature. The decanted organic phase was washed with water, dried over sodium sulfate and vacuum filtered. The filter was rinsed and the filtrate was evaporated to dryness to obtain 14.3 g of residue. The latter was chromatographed over silica gel and eluted with an 8-2 hexane-ethyl acetate mixture and then a 9-1 hexane-ethyl acetate mixture to obtain 7.8 g of (2R)(6-bromo-hexahydro-3,5-methano-2H-cyclopenta[b]furano-2-yl)-oxy (S)α-cyano-3-phenoxy-benzyl melting at 65° C. and having a specific rotation of $[\alpha]_D^{20} = -108°$ (c=0.5% in dimethylformamide) and 3 g of the corresponding (2S) isomer with a specific rotation of $[\alpha]_D^{20} = +105.5°$ (c=0.5% in dimethylformamide).

EXAMPLE 10

(R,S)α and (R)α and (S)α-[(2S)(6-bromo-hexahydro-3,5-methano-2H-cyclopenta[b]furan-2-yl)-oxy]-3-phenoxy-benzene-acetonitrile STEP A: (2S) 6-bromo-hexahydro-3,5-methano-2H-cyclopenta[b]-2-[(3R)-(4,4-dimethyl-2-oxo-tetrahydrofuran-3-yl)-oxy]-furan A mixture of 46.33 g of D(−) 2-oxo-4,4-dimethyl-3-hydroxy-tetrahydrofuran, 460 ml of methylene chloride and 460 mg of p-toluene sulfonic acid was refluxed while a solution of 60 g of racemic 6-bromo-hexahydro-3,5-methano-2H-cyclopenta[b]furan-2-ol in 360 ml of methylene chloride was added thereto and the mixture was refluxed for 2 hours with stirring to remove the water of reaction. The mixture was cooled to room temperature and the decanted organic phase was washed with water, dried, vacuum filtered and evaporated to dryness under reduced pressure. The 94.7 g of residue were chromatographed over silica gel and eluted with a 8-2 hexane-ethyl acetate mixture to obtain (2S) 6-bromo-hexahydro-3,5-methano-2H-cyclopenta[b]-2-[(3R)-(4,4-dimethyl-2-oxo-tetrahydrofuran-3-yl)-oxy]-furan melting at 178° C. and having a specific rotation of $[\alpha]_D^{20} = +156°$ (c=1% in dimethylformamide) and the corresponding (2R) isomer melting at 104° C. and having a specific rotation of $[\alpha]_D^{20} = -122°$ (c=1% in dimethylformamide).

STEP B: (2S) 6-bromo-hexahydro-3,5-methano-2H-cyclopenta[b]furan-2-ol

A mixture of 4.2 g of the (2S) isomer of Step A, 40 ml of dioxane, 20 ml of water and 500 mg of p-toluene sulfonic acid was refluxed with stirring for 17 hours and was cooled to room temperature and diluted with water. The mixture was extracted with methylene chloride and the organic phase was washed with water, dried and evaporated to dryness under reduced pressure. The 3.2 g of residue were chromatographed over silica gel and eluted with a 7-3 hexane-ethyl acetate mixture to obtain (2S) 6-bromo-hexahydro-3,5-methano-2H-cyclopenta[b]furan-2-ol melting at 61° C. and having a specific rotation of $[\alpha]_D^{20} = +133°$ (c=0.75% in dimethylformamide).

STEP C: (R,S)α and (R)α and (S)α[(2S)(6-bromo-hexahydro-3,5-methano-2H-cyclopenta[b]furan-2-yl)-oxy]-3-phenoxy-benzene acetonitrile A solution of 2.19 g of the product of Step B in 50 ml of methylene chloride was added to a refluxing mixture of 2.93 g of (R,S)α-cyano-3-phenoxy-benzyl alcohol, 100 ml of methylene chloride and 300 mg of p-toluene sulfonic acid and the mixture was refluxed for another 15 minutes and then returned to room temperature. The mixture was washed with water, dried, vacuum filtered and evaporated to dryness under reduced pressure. The 4.34 g of the (R,S)α-[(2S)(6-bromohexahydro-3,5-methano-2H-cyclopenta[b]furan-2-yl)-oxy]-3-phenoxy-benzene acetonitrile were chromatographed over silica gel and eluted with a 9-1 hexane-ethyl acetate mixture to obtain the (S)α-isomer melting at 65° C. and having a specific rotation of $[\alpha]_D^{20} = +110°$ (c=0.5% in dimethylformamide) and the (R)α-isomer with a specific rotation of $[\alpha]_D^{20} = +108.5°$ (c=0.4% in dimethylformamide).

EXAMPLE 11

(2S,3S,3aS,5R,6aS)(hexahydro-3,5-methano-2H-cyclopenta[b]furan-2-yl)-oxy-(S)α-cyano-3-phenoxy-benzyl

STEP A: (2R) hexahydro-3,5-methano-2H-cyclopenta[b]furan-2-ol

A mixture of 371 mg of (2R)(6-bromo-hexahydro-3,5-methano-2H-cyclopenta[b]furan-2-yl)-oxy-(S)α-cyano-3-phenoxy-benzyl, 5 ml of benzene and 300 mg of tributyl tin hydride was refluxed for 17 hours and was then diluted with ether. The mixture was stirred with aqueous 10% potassium fluoride solution and the organic phase was washed with water, dried and evaporated to dryness under reduced pressure. The 380 mg of residue were chromatographed over silica gel and were eluted with a 9-1 hexane-ethyl acetate mixture to obtain (2S,3S,3aS,5R,6aS)(hexahydro-3,5-methanol-2H-cyclopenta[b]furan-2-yl)-oxy (S)α-cyano-3-phenoxy-benzyl melting at 48° C. and having a specific rotation of $[\alpha]_D^{20} = -121°$ (c=0.5% in dimethylformamide). The latter was hydrolyzed as in Step B of Example 10 to obtain (2R) hexahydro-3,5-methano-2H-cyclopenta[b]furan-2-ol.

STEP B: (2S,3S,3aS,5R,6aS)(hexahydro-3,5-methano-2H-cyclopenta[b]furan-2-yl)-oxy-(S)α-cyano-3-phenoxy-benzyl Using the procedure of Step C of Example 10, the product of Step A and (S)α-cyano-3-phenoxy-benzyl alcohol were reacted to obtain (2S,3S,3aS,5R,6aS)(hexahydro-3,5-methano-2H-cyclopenta[b]furan-2-yl)-oxy-(S)α-cyano-3-phenoxy-benzyl melting at 48° C. and having a specific rotation of $[\alpha]_D^{20} = -121°$ (c=0.5% in dimethylformamide).

EXAMPLE 12

(2R,3R,3aR,5S,6aR)(hexahydro-3,5-methano-2H-cyclopenta[b]furan-2-yl)-oxy-(S)α-cyano-3-phenoxy-benzyl Using the procedure of Step A of Example 11, the corresponding (2S) 6-bromo compound was reacted to obtain (2R,3R,3aR,5S,6aR)(hexahydro-3,5-methano-2H-cyclopenta[b]furan-2-yl)-oxy (S)α-cyano-3-phenoxy-benzyl melting at <45° C. and having a specific rotation of $[\alpha]_D^{20} = +92.5°$ (c=0.5% in dimethylformamide) which was hydrolyzed to form (2S) hexahydro-3,5-methano-2H-cyclopenta[b]furan-2-ol. The latter compound was reacted with (S)α-cyano-3-phenoxy-benzyl alcohol as in Step B of Example 11 to obtain (2R,3R,3aR,5S,6aR)(hexahydro-3,5-methano-2H-cyclopenta[b]furan-2-yl-oxy-(S)α-cyano-3-phenoxy-benzyl melting at <45° C. and having a specific rotation of $[\alpha]_D^{20} = +92.5°$ (c=0.5% in dimethylformamide).

EXAMPLE 13

(1R,2R,5S)6,6-dimethyl-3-oxa-2-[(R) and (S)cyano-(6-phenoxy-2-pyridyl)-methoxy-bicyclo[3,1,0]hexane A mixture of 2.59 g of (1R,2S,5S) 6,6-dimethyl-3-oxa-bicyclo[3,1,0]hexan-2-ol, 4 g of racemic cyano-(6-phenoxy-2-pyridyl)-methanol, 18 mg of p-toluene sulfonic acid and 50 ml of methylene chloride was stirred at 20° C. for 17 hours and was then refluxed under reduced pressure to remove water by azeotropic distillation. Sodium bicarbonate was added to the stirred mixture which was then evaporated to dryness under reduced pressure. The residue was chromatographed over silica gel and eluted with an 8-2 petroleum ether (b.p.=35°-70° C.)-ether mixture to obtain 2.5 g of (1R,2R,5S) 6,6-dimethyl-3-oxa-2-[(R)cyano-(6-phenoxy-2-pyridyl)-methoxy]-bicyclo[3,1,0]hexane with a specific rotation of $[\alpha]_D^{20} = +95.5°$ (c=0.9% in benzene) and 2.45 g of the corresponding (S) isomer with a specific rotation of $[\alpha]_D^{20} = +69.6°$ (c=0.9% in benzene).

NMR Spectrum (deuterochloroform):

(R) isomer: Peaks at 1.03 ppm (hydrogens of geminal methyls); at 3.6 to 4.0 ppm (hydrogens of —OCH$_2$—); at 5.2 and 5.4 ppm (hydrogen of —OCH—); at 6.8–6.9 ppm (3- and 5-hydrogens of pyridyl); at 7.6–7.7–7.8 ppm (4-hydrogen of pyridyl).

(S) isomer: Peaks at 1.0–1.03 ppm (hydrogens of geminal methyls); at 3.75–3.89 ppm and 4.12–4.25 ppm (hydrogens of

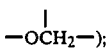

—OCH$_2$—);

at 5.0 and 5.3 ppm (hydrogen of

—OCH—);

at 6.75–6.9 ppm (3- and 5-hydrogens of pyridyl); at 7.6–7.7–7.8 ppm (4-hydrogen of pyridyl).

EXAMPLE 14

(1R,2R,5S) 6,6-dimethyl-3-oxa-2-[(R) and (S)cyano(3-phenoxy-4-fluoro-phenyl)-methoxy]-bicyclo(3,1,0)hexane A mixture of 16 g of (R,S)α-cyano-4-fluoro-3-phenoxy-benzyl alcohol, 100 ml of dichloromethane, 9.4 g of (1R,2S,5S) 6,6-dimethyl-3-oxa-bicyclo(3,1,0)hexane-2-ol and 0.1 g of p-toluene sulfonic acid was refluxed for 90 minutes and was then poured into dilute aqueous sodium bicarbonate solution. The organic phase was evaporated to dryness under reduced pressure and the 25.06 g of (1R,2R,5S) 6,6-dimethyl-3-oxa-2-[(R,S)-cyano-(3-phenoxy-4-fluoro-phenyl)-methoxy]-bicyclo(3,1,0)hexane were chromatographed over silica gel. Elution with an 8-2 hexane-ether mixture yielded 8.85 g of the corresponding (R) isomer melting at less than 50° C. and having a specific rotation of $[\alpha]_D^{20} = +102°$ (c=1% in benzene) and 9.05 g of the corresponding (S) isomer melting at 65° C. and having a specific rotation of $[\alpha]_D^{20} = +50°$ (c=0.4% in benzene).

| Circular dichroism (dioxane): | | |
| --- | --- | --- |
| (R) isomer: | max. at 279 nm | Δε = −0.27 |
| (S) isomer: | Inflexion towards 275 nm | Δε = +0.13 |
| | max. at 281 nm | Δε = +0.15 |

NMR Spectrum (deuterochloroform):

(R) isomer: Peaks at 1.07 ppm (hydrogens of geminal methyls); at 1.33–1.78 ppm (hydrogens of cyclopropyl);

at 3.7–4.1 ppm (hydrogens of —CH₂O—); at 5.2–5.5 ppm (hydrogen of

);

at 6.9–7.6 ppm (aromatic hydrogens).

(S) isomer: Peaks at 1.0 ppm (hydrogens of geminal methyls); at 1.55–1.57 ppm (hydrogens of cyclopropyl); at 3.8–3.9 ppm and 4.1–4.3 ppm (hydrogens of —CH₂O—); at 4.9–5.3 ppm (hydrogen of

);

at 6.9–7.6 ppm (aromatic hydrogens).

EXAMPLES 15 TO 24

Using the procedure of the foregoing examples, the corresponding lactol of formula III and the alcohol of formula IV were reacted to obtain the compounds of formula I indicated in the following Table in the form of their diasterisomers which could be separated by classical crystallization and chromatography procedures.

)hexane of Example 1, 10 ml of methanol and 0.1 g of p-toluene sulfonic acid was stirred at 20° C. for 2 hours and was then diluted with water. The mixture was extracted with methylene chloride and the organic phase was evaporated to dryness under reduced pressure. The residue was chromatographed over silica gel and eluted with a 7-3 hexane-ethyl acetate mixture to obtain (S)α-cyano-3-phenoxy-benzyl alcohol with a specific rotation of $[\alpha]_D^{20} = -16.5°$ (c=0.8% in benzene).

The same procedure was repeated starting with 1 g of (1R,2R,5S)6,6-dimethyl-3-oxa-2-[(R)cyano-(3-phenoxy-phenyl)-methoxy]-bicyclo(3,1,0)hexane of Example 1 to obtain (R)α-cyano-3-phenoxy-benzyl alcohol with a specific rotation of $[\alpha]_D^{20} = +16.5°$ (c=0.8% in benzene).

EXAMPLE 26

(S) and (R)α-cyano-3-phenoxy-4-fluoro-benzyl alcohol

A mixture of 9 g of (1R,2R,5S)6,6-dimethyl-3-oxa-2-[(R)cyano-(3-phenoxy-4-fluoro-phenyl)-methoxy]-bicyclo(3,1,0)hexane from Example 14, 100 ml of methanol and 90 mg of p-toluene sulfonic acid was stirred at 20° C. for 90 minutes and was then poured into water. The mixture was extracted with chloroform and the organic phase was evaporated to dryness under reduced pres-

TABLE

| Example No. | Final Product | Physical Properties |
|---|---|---|
| 15 | (1R,2S,4R,5S) 6,6-dimethyl-4-trichloromethyl-2-[(1S) 2-methyl-4-oxo-3-(2-propen-1-yl)-cyclopent-2-enyloxy]-3-oxa-bicyclo (3,1,0) hexane | melting point = 90° C. |
| 16 | (1R,2S,4R,5S) 6,6-dimethyl-4-trichloromethyl-2-[(1R) 2-methyl-4-oxo-3-(2-propen-1-yl)-cyclopent-2-enyloxy]-3-oxa-bicyclo (3,1,0) hexane | melting point = 128° C. |
| 17 | (1R,2S,4R,5S) 6,6-dimethyl-4-trichloromethyl-2-[(R,S)-cyano-(3-phenoxy-phenyl)-methoxy]-3-oxa-bicyclo (3,1,0) hexane which was separated as (R) and (S) isomers | both isomers were oils |
| 18 | (1R,2S,4R,5S) 6,6-dimethyl-4-tribromomethyl-2-[(1S) 2-methyl-4-oxo-3-(2-propen-1-yl)-cyclopent-2-enyloxy]-3-oxa-bicyclo (3,1,0) hexane | Oil $[\alpha]_D^{20} = +72° \pm 3°$ (c = 0.6% benzene) |
| 19 | (11R,12S,15S) and (11S,12R,15R) 12-[(S) (1-methyl)-heptyloxy]-9,10,11,12,14,15-hexahydro-9,10 [3',4'] furano-anthracene | (11R,12S,15S) isomer: $[\alpha]_D^{20} = +88° \pm 2.5°$ (c = 1% in dimethylformamide) (11S,12R,15R) isomer: $[\alpha]_D^{20} = -76.5° \pm 2°$ (c = 1% in dimethylformamide) |
| 20 | (11R,12S,15S) 12-[(1S) and (1R) 2-methyl-4-oxo-3-(2-propen-1-yl)-cyclopent-2-enyloxy]-9,10,11,12,14,15-hexahydro-9,10 [3',4'] furano-anthracene | (1S) isomer: m.p. = 164° C.; $[\alpha]_D^{20} = -98°$ (c = 1% in dimethylformamide). (1R) isomer: m.p. = 182° C.; $[\alpha]_D^{20} = -133°$ (c = 1% in dimethylformamide). |
| 21 | (11S,12R,15R) 12-[(R) and (S) 1-phenylethoxy]-9,10,11,12,14,15-hexahydro-9,10 [3',4'] furano-anthracene | (R) isomer: m.p. = 152° C.; $[\alpha]_D^{20} = +155°$ (c = 0.9% in dimethylformamide) (S) isomer: m.p. = 126° C.; $[\alpha]_D^{20} = +50°$ (c = 0.5% in dimethylformamide) |
| 22 | (11R,12S,15S) 12-[(R) and (S) 3-pinanyl-methoxy]-9,10,11,12,14,15-hexahydro-9,10 [3',4'] furano-anthracene | (R) isomer: m.p. = 178° C.; $[\alpha]_D^{20} = +58°$ (c = 0.5% in dimethylformamide) (S) isomer: m.p. = 148° C.; $[\alpha]_D^{20} = +100°$ (c = 0.5% in dimethylformamide) |
| 23 | (11R,12S,15S) 12-[(S) and (R) 2-methyl-butyloxy]-9,10,11,12,14,15-hexahydro-9,10 [3',4'] furano-anthracene | (S) isomer: m.p. = 112° C.; $[\alpha]_D^{20} = +90°$ (c = 0.8% in dimethylformamide) (R) isomer: m.p. = 85° C.; $[\alpha]_D^{20} = +88.5°$ (c = 0.5% in dimethylformamide) |
| 24 | (11S,12R,15R) 12-[(S) and (R) 1-methylbutyloxy]-9,10,11,12,14,15-hexahydro-9,10 [3',4'] furano-anthracene | (S) isomer: m.p. = 122° C.; $[\alpha]_D^{20} = +111°$ (c = 0.5% in dimethylformamide) (R) isomer: m.p. = 105° C.; $[\alpha]_D^{20} = +90.5°$ (c = 0.25% in dimethylformamide) |

The following examples illustrate the use of the compounds of formula I to prepare the optically active isomers of formula III and the optically active isomers of the alcohols of formula IV.

EXAMPLE 25

(R) and (S)α-cyano-3-phenoxy-benzyl alcohol

A mixture of 1 g of (1R,2R,5S)6,6-dimethyl-3-oxa-2-[(S)cyano-(3-phenoxy-phenyl)-methoxy]-bicyclo(3,1,0- sure. The residue was chromatographed over silica gel and was eluted with a 7-3 hexane-ethyl acetate mixture containing 1% of acetic acid to obtain 4.9 g of (R)α-cyano-3-phenoxy-4-fluoro-benzyl alchol with a specific rotation of $[\alpha]_D^{20} = +26.5° \pm 2.5°$ (c=0.5% in pyridine).

The procedure was repeated with 9 g of (1R,2R,5S)6,6-dimethyl-3-oxa-2-[(S)cyano-(3-phenoxy- 4-fluoro-phenyl)-methoxy]-bicyclo(3,1,0)hexane of Example 14 to obtain 4.5 g of (S)α-cyano-3-phenoxy-4-fluoro-benzyl alcohol with a specific rotation of $[\alpha]_D^{20} = -30° \pm 2.5°$ (c=0.5% in pyridine).

EXAMPLE 27

(S) and (R)cyano-(6-phenoxy-2-pyridyl)-methanol

A mixture of 13.4 g of (1R,2R,5S)6,6-dimethyl-3-oxa-2-[(R)cyano-(6-phenoxy-2-pyridyl)-methoxy]-bicyclo(3,1,0)hexane of Example 13, 200 ml of methanol and 150 mg of p-toluene sulfonic acid was stirred at 20° C. for 90 minutes and was then poured into ice and water. The mixture was vacuum filtered to obtain 8 g of (R)cyano-(6-phenoxy-2-pyridyl)-methanol melting at 95° C. and having a specific rotation of $[\alpha]_D^{20} = -63.5°$ (c=1% in pyridine) and +82° (c=1% in benzene).

The procedure was repeated with 13.4 g of (1R,2R,5S)6,6-dimethyl-3-oxa-2-[(S)cyano-(6-phenoxy-3-pyridyl)-methoxy]-bicyclo(3,1,0)hexane of Example 13 to obtain 8 g of (S) cyano-(6-phenoxy-2-pyridyl)-methanol melting at 95° C. and having a specific rotation of $[\alpha]_D^{20} = +62.5°$ (c=1% in pyridine) and −80° (c=1% in benzene).

EXAMPLE 28

Using the procedure of Example 25, the appropriate isomer of Example 3 was hydrolyzed to obtain (R) allethrolone with a specific rotation of $[\alpha]_D^{20} = -14°$ (c=2% in chloroform) and (1R,2S,4R,5S)6,6-dimethyl-4-trichloromethyl-3-oxa-bicyclo(3,1,0)hexan-2-ol melting at 140° C.

EXAMPLE 29

Using the procedure of Example 25, the appropriate isomer of Example 4 was hydrolyzed to obtain (R) allethrolone with a specific rotation of $[\alpha]_D^{20} = -16°$ (c=0.9% in chloroform) and (1R,2S,4R,5S)6,6-dimethyl-4-trichloromethyl-3-oxa-bicyclo(3,1,0)hexan-2-ol melting at 100° to 105° C.

EXAMPLE 30

Using the procedure of Example 25, the appropriate isomer of Example 6 was hydrolyzed to obtain (S)α-cyano-3-phenoxy-benzyl alcohol with a specific rotation of $[\alpha]_D^{20} = -30°$ C.±1° (c=1% in carbon tetrachloride) and (11R,12R,15S)9,10,11,12,14,15-hexahydro-9,10[3',4']furano-anthracene-12-ol melting at 160° C. and having a specific rotation of $[\alpha]_D^{20} = -44°$ (c=0.9% in dimethylformamide).

EXAMPLE 31

Using the procedure of Example 25, the appropriate isomer of Example 19 was hydrolyzed to obtain (S)-octanol and (11R,12R,15S)9,10,11,12,14,15-hexahydro-9,10[3',4']furano-anthracene-12-ol melting at 160° C. and having a specific rotation of $[\alpha]_D^{20} = -38°$ (c=1% in dimethylformamide).

EXAMPLE 32

Using the procedure of Example 25, the appropriate isomer of Example 10 was hydrolyzed to obtain (R)α-cyano-3-phenoxy-benzyl alcohol with a specific rotation of $[\alpha]_D^{20} = +26.5°$ (c=1% in CCl₄) and (2S)6-bromo-hexahydro-3,5-methano-2H-cyclopenta[b]furan-2-ol.

EXAMPLE 33

Using the procedure of Example 25, the appropriate isomer of Example 9 was hydrolyzed to obtain (S)α-cyano-3-phenoxy-benzyl alcohol with a specific rotation of $[\alpha]_D^{20} = -31°$ (c=0.5% in CCl₄) and (2S) 6-bromo-hexahydro-3,5-methano-2H-cyclopenta[b]furano-2-ol melting at 61° C. and having a rotation of $[\alpha]_D^{20} = +133.6°$ (c=0.5% in dimethylformamide).

EXAMPLE 34

Using the procedure of Example 25, the appropriate isomer of Example 9 was hydrolyzed to obtain (S)α-cyano-3-phenoxy-benzyl alcohol with a specific rotation of $[\alpha]_D^{20} = -26.5°$ (c=1% in CCl₄) and (2R)6-bromo-hexahydro-3,5-methano-2H-cyclopenta[b]furan-2-ol melting at 61° C. and having a specific rotation of $[\alpha]_D^{20} = -134°$ (c=1% in dimethylformamide).

Various modifications of the processes and products of the invention may be made without departing from the spirit or scope thereof and it should be understood that the invention is intended to be limited only as defined in the appended claims.

What we claim is:

1. A hemiacetal in all possible isomeric forms of the formula

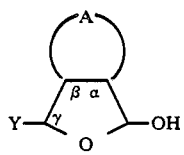

III wherein A, represents an optionally substituted hydrocarbon chain selected from the group consisting of

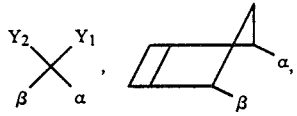

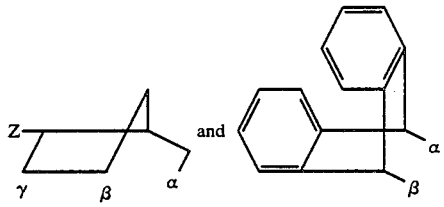

wherein
Y₁ and Y₂ are individually selected from the group consisting of hydrogen, fluorine, chlorine, bromine and alkyl of 1 to 6 carbon atoms, or Y₁ and Y₂ together with the carbon to which they are attached form a carbon homocycle of 3 to 7 carbon atoms; and
Z is selected from the group consisting of hydrogen, chlorine, bromine and iodine;
Y is selected from the group consisting of alkyl of 1 to 18 carbon atoms optionally substituted with a halogen; and
—CY₃' and a β,γ bond together with Y may be included in A and Y' is bromine or chlorine.

2. A hemiacetal in all possible isomeric forms of the formula

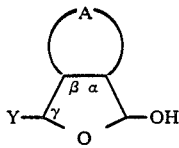

wherein A, of which β,γ bond can be part, represents an optionally substituted hydrocarbon chain selected from the group consisting of

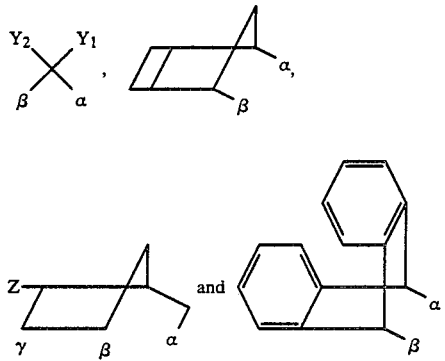

wherein $Y_1$ and $Y_2$ are individually selected from the group consisting of hydrogen, fluorine, chlorine, bromine and alkyl of 1 to 6 carbon atoms, or $Y_1$ and $Y_2$ together with the carbon to which they are attached form a carbon homocycle of 3 to 7 carbon atoms and Z is selected from the group consisting of hydrogen, chlorine, bromine and iodine.

3. A compound of claim 1 seleted from the group consisting of (1R,2S,4R,5S)6,6-dimethyl-4-[2-methyl-2-propyl]-3-oxa-bicyclo(3,1,0)hexa-2-ol and its antipodal form, (1R,2S,4R,5S)6,6-dimethyl-4-trichloromethyl-3-oxa-bicyclo(3,1,0)hexan-2-ol and its antipodal form and (1R,2S,4R,5S)6,6-dimethyl-4-tribromo-methyl-3-oxa-bicyclo(3,1,0)hexan-2-ol and its antipodal form.

4. A compound of claim 2 selected from the group consisting of (1R,2S,5S)6,6-dimethyl-3-oxa-bicyclo-(3,1,0)hexan-2-ol and its antipodal form, (3aR,4R,7S,7aS,1S)tetrahydro-4,7-methano-isobenzofuran-1-ol and its antipodal form, racemic 9,10,11,12,14,15-hexahydro-9,10-[3',4']-furananthracene-12-ol, (11R,12R,15S)9,10,11,12,14,15-hexahydro-9,10,-[3',4']furananthracene-12-ol and its antipodal form, racemic 6-bromohexahydro-3,5-methano-2H-cyclopenta[b]furan-2-ol, (2S,3S,3aR,5S,6S,6aS)6-bromo-hexahydro-3,5-methano-2H-cyclopenta[b]furan-2-ol and its antipodal form and (2S,3R,3aR,5S,6aR)hexahydro-3,5-methano-2H-cyclopenta[b]furan-2-ol and its antipodal form.

* * * * *